(12) United States Patent
Sakamoto et al.

(10) Patent No.: US 9,606,040 B2
(45) Date of Patent: Mar. 28, 2017

(54) SENSOR CONTROLLER

(75) Inventors: Yuuki Sakamoto, Kariya (JP);
Mikiyasu Matsuoka, Kariya (JP);
Yuuzou Matsumoto, Kariya (JP)

(73) Assignee: DENSO CORPORATION, Kariya (JP)

( * ) Notice: Subject to any disclaimer, the term of this patent is extended or adjusted under 35 U.S.C. 154(b) by 455 days.

(21) Appl. No.: 13/183,810

(22) Filed: Jul. 15, 2011

(65) Prior Publication Data
US 2012/0031169 A1 Feb. 9, 2012

(30) Foreign Application Priority Data

Aug. 6, 2010 (JP) ................. 2010-177514

(51) Int. Cl.
*F01N 3/023* (2006.01)
*G01N 33/00* (2006.01)
*G01N 15/06* (2006.01)
*F02D 41/14* (2006.01)
*F02D 41/22* (2006.01)

(52) U.S. Cl.
CPC ..... *G01N 15/0656* (2013.01); *F02D 41/1466* (2013.01); *F02D 41/222* (2013.01); *Y02T 10/40* (2013.01)

(58) Field of Classification Search
CPC .............. F02D 41/1466; F02D 41/222; G01N 15/0656; F01N 11/00; F01N 13/008; F01N 2550/00; Y02T 10/47; Y02T 10/40
USPC ................. 73/865.9, 1.06; 324/71.4
See application file for complete search history.

(56) References Cited

U.S. PATENT DOCUMENTS

| 4,656,832 A | 4/1987 | Yukihisa et al. |
| 2002/0060150 A1* | 5/2002 | Hashimoto et al. .......... 204/401 |
| 2008/0264045 A1* | 10/2008 | Hara ................... F01N 3/0222 60/295 |
| 2010/0147052 A1* | 6/2010 | Nelson et al. ............... 73/28.01 |

(Continued)

FOREIGN PATENT DOCUMENTS

JP 2010-151059 7/2010

OTHER PUBLICATIONS

Office Action (2 pages) dated Jul. 23, 2013, issued in corresponding Japanese Application No. 2010-177514 and English translation (3 pages).

*Primary Examiner* — Helen Kwok
*Assistant Examiner* — Nashmiya Fayyaz
(74) *Attorney, Agent, or Firm* — Nixon & Vanderhye P.C.

(57) ABSTRACT

A sensor controller is applied to a particulate matter detection sensor that includes an attachment portion to which conductive particulate matter contained in gas is attached, and a pair of opposed electrodes spaced from each other at the attachment portion. The particulate matter detection sensor is adapted to output a detection signal corresponding to a resistance between the pair of opposed electrodes, and the sensor controller is adapted to calculate an amount of attached particulate matter based on a sensor detection value from the particulate matter detection sensor. The sensor controller includes a heater for heating the attachment portion so as to burn and remove the particulate matter attached to the attachment portion, and an abnormality diagnosis portion for obtaining the sensor detection value during a heating of the heater and for performing diagnosis of abnormality of the particulate matter detection sensor based on the obtained sensor detection value.

7 Claims, 9 Drawing Sheets

(56) References Cited

U.S. PATENT DOCUMENTS

2010/0312488 A1* 12/2010 Diehl et al. .................... 702/23
2011/0047978 A1* 3/2011 Zawacki et al. ............... 60/277
2011/0109331 A1* 5/2011 Nelson et al. ............... 324/693
2012/0119759 A1* 5/2012 Nelson et al. ............... 324/691

* cited by examiner

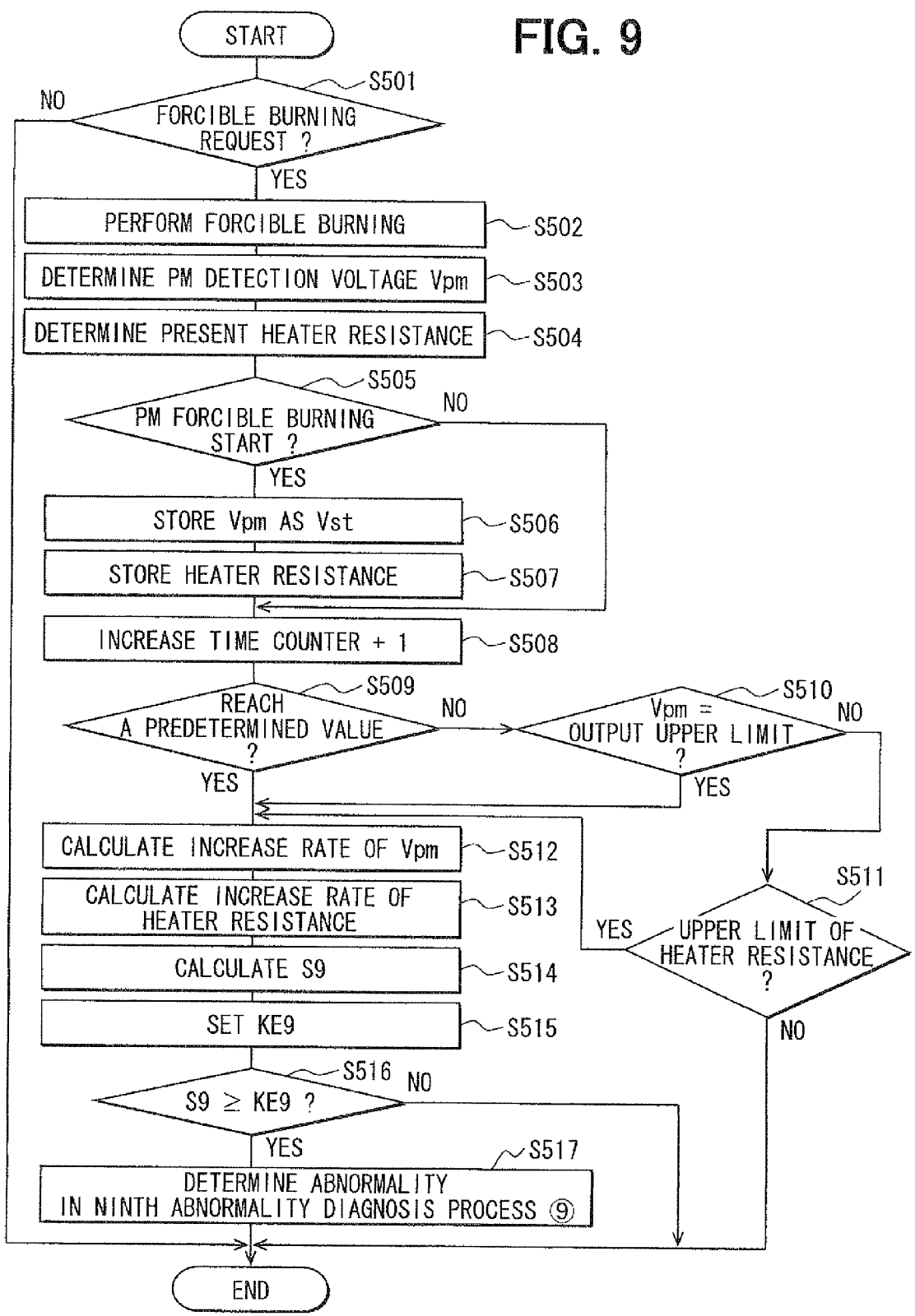

SENSOR CONTROLLER

CROSS REFERENCE TO RELATED APPLICATION

This application is based on Japanese Patent Application No. 2010-177514 filed on Aug. 6, 2010, the contents of which are incorporated herein by reference in its entirety.

TECHNICAL FIELD

The present invention relates to a sensor controller for calculating an amount of particulate matter (PM) based on a detection signal from a particulate matter detection sensor.

BACKGROUND

Various types of PM sensors (particulate matter detection sensors) for detecting the amount of PM exhausted from an engine or the like have been proposed. For example, a PM sensor disclosed in JP 59-196453A (corresponding to U.S. Pat. No. 4,656,832) includes a pair of opposed electrodes on an insulating substrate. The accumulation of PM changes a resistance between the pair of the electrodes. By using this property, the PM sensor is configured to detect the amount of PM by measuring the resistance between the electrodes. In this case, a signal output circuit connected to a sensor element forms a voltage-dividing circuit configured by a resistance between the pair of opposed electrodes and a predetermined shunt resistance. The signal output circuit is configured to output a voltage at an intermediate point of the voltage-dividing circuit as a sensor detected signal.

A sensor detection value obtained from the PM sensor often deviates from a normal value due to the deterioration of the PM sensor with time, or the failure or the like of the signal output circuit connected to the PM sensor, thereby disadvantageously resulting in wrong detection of the amount of accumulated PM. In such a case, the wrong detection of the amount of accumulated PM adversely affects various types of control processes to be performed using the result of the detection.

SUMMARY

In view of the foregoing matter, it is an object of the invention to provide a sensor controller that can appropriately detect an abnormality of a PM sensor.

According to an aspect of the present invention, a sensor controller is applied to a particulate matter detection sensor that includes an attachment portion to which conductive particulate matter contained in gas is attached, and a pair of opposed electrodes spaced from each other at the attachment portion. The particulate matter detection sensor is adapted to output a detection signal corresponding to a resistance between the pair of opposed electrodes, and the sensor controller is adapted to calculate an amount of attached particulate matter based on a sensor detection value from the particulate matter detection sensor. Furthermore, the sensor controller includes a heater configured to heat the attachment portion so as to burn and remove the particulate matter attached to the attachment portion, and abnormality diagnosis means for obtaining the sensor detection value during a heating of the heater and for performing diagnosis of abnormality of the particulate matter detection sensor based on the obtained sensor detection value. As a result, the abnormality of the particulate matter detection sensor can be appropriately detected.

For example, a signal output circuit may be connected to the particulate matter detection sensor, and the sensor detection value may be changeable by the signal output circuit within a predetermined output range. The sensor controller further includes means for calculating a reaching time period required from the start of the heating of the heater to a time where the sensor detection value reaches a limit of the predetermined output range. In this case, the abnormality diagnosis means may perform the diagnosis of abnormality of the particulate matter detection sensor based on the reaching time period.

Alternatively, the sensor controller may include means for calculating a holding time period required from when the sensor detection value reaches the limit of the predetermined output range after the start of the heating of the heater to when the sensor detection value begins to decrease from the limit of the predetermined output range. In this case, the abnormality diagnosis means performs the diagnosis of abnormality of the particulate matter detection sensor based on the holding time period. Alternatively, the sensor controller may include means for calculating a decreasing start time at which the sensor detection value begins to decrease from the limit of the predetermined output range, after the start of the heating of the heater. In this case, the abnormality diagnosis means performs the diagnosis of abnormality of the particulate matter detection sensor based on the decreasing start time.

BRIEF DESCRIPTION OF THE DRAWINGS

Other objects, features and advantages of the present invention will become more apparent from the following description made with reference to the accompanying drawings, in which like parts are designated by like reference numbers and in which:

FIG. 9 is a flowchart showing a ninth abnormality diagnosis process; and

DETAILED DESCRIPTION OF THE PREFERRED EMBODIMENTS

Figure 1:
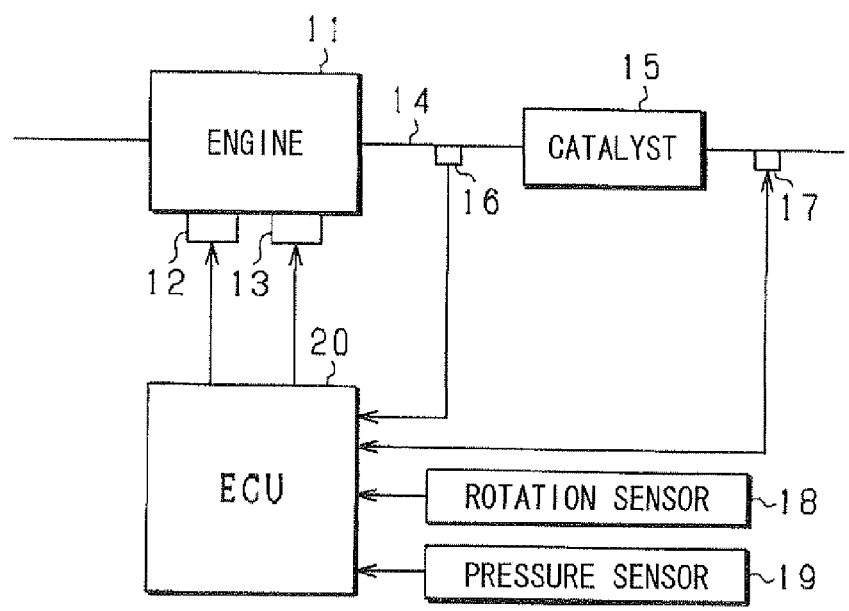
FIG. 1 is a schematic configuration diagram showing the outline of an engine control system according to an embodiment of the invention.

Hereinafter, an embodiment of the present invention will be described on the basis of the drawings. In this embodiment, a vehicle engine system with a vehicle-mounted engine is provided to monitor the amount of PM (amount of conductive particulate matter) of exhaust gas exhausted from an engine. In particular, a PM sensor is provided in an engine exhaust pipe. Based on the amount of attached PM detected by the PM sensor, the amount of PM is monitored. FIG. 1 shows a configuration diagram of the outline of the system.

In FIG. 1, an engine 11 is a direct-injection gasoline engine. The engine 11 is provided with a fuel injection valve 12 and an igniter 13 which serve as an actuator for the operation of the engine 11. An exhaust pipe 14 of the engine 11 is provided with a three way catalyst 15 serving as an exhaust emission control system. An A/F sensor 16 is provided at an upstream side of the three way catalyst 15, and a PM sensor 17 as a particulate matter detection sensor is provided at a downstream side of the three way catalyst 15. The system is further provided with a rotation sensor 18 for detecting an engine rotational speed, a pressure sensor 19 for detecting the pressure of an intake pipe, and the like.

An ECU 20 mainly includes a microcomputer constructed of a well-known CPU, ROM, RAM, and the like, The ECU executes various control programs stored in the ROM to perform various control processes of the engine 11, based on the operating state of the engine. That is, the ECU 20 receives input of respective signals from the above sensors or the like, and controls the driving of the fuel injection valve 12 and the igniter 13 by computing the amount of injected fuel or the ignition timing based on the respective signals received.

The ECU 20 calculates the amount of PM actually exhausted from the engine 11 (actual PM emission amount) based on a detection signal from the PM sensor 17, and makes a diagnosis of the combustion state of the engine 11 based on the actual PM emission amount. Specifically, when the actual PM emission amount exceeds a predetermined value for determination of abnormality, it is determined that the amount of exhausted PM is excessive and that the engine becomes abnormal.

Further, the ECU 20 may variably control the control state of the engine 11 based on the actual PM emission amount calculated from the detection result of the PM sensor 17. For example, the ECU 20 can control the amount of injected fuel, the injection timing of fuel, and the ignition timing, based on the actual PM emission amount.

Figure 2:
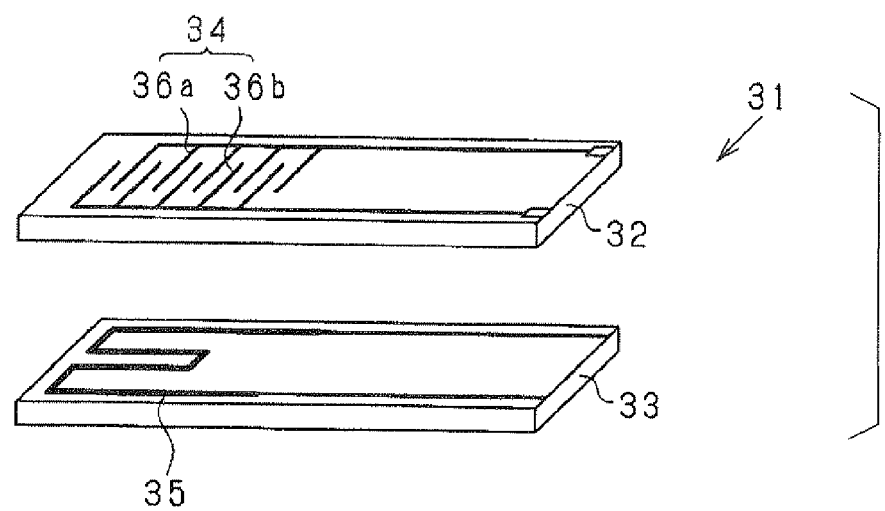
FIG. 2 is an exploded perspective view showing a main structure of a sensor element in a PM sensor.
Figure 3:
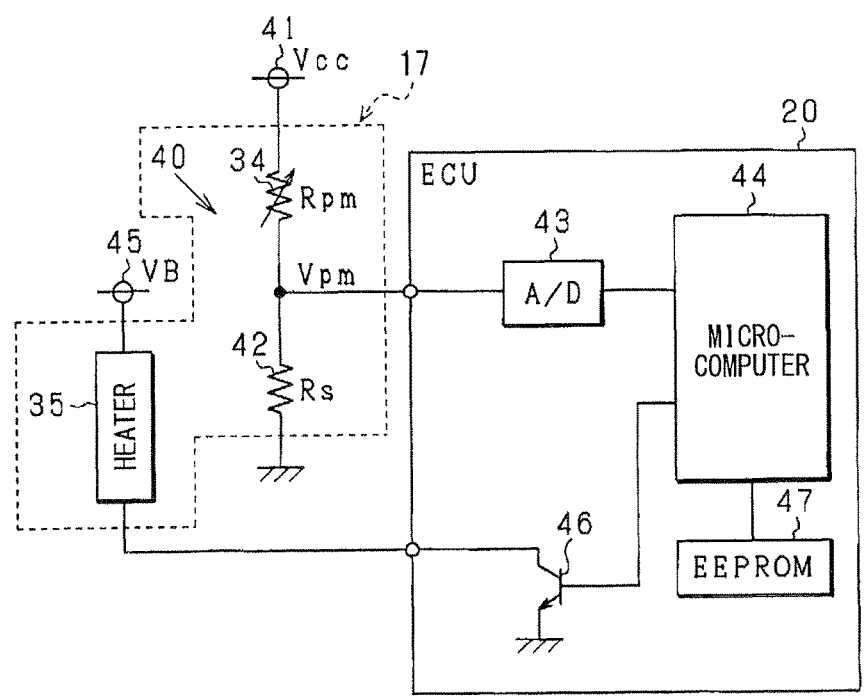
FIG. 3 is an electric configuration diagram regarding the PM sensor.

Next, the structure of the PM sensor 17, and the electric configuration of the PM sensor 17 will be described using FIGS. 2 and 3. FIG. 2 shows an exploded perspective view of the main structure of a sensor element 31 configured in the PM sensor 7, and FIG. 3 shows an electric configuration diagram regarding the PM sensor 17.

As shown in FIG. 2, the sensor element 31 includes two pieces of insulating substrates 32 and 33 having a longitudinal plate shape. One insulating substrate 32 is provided with a PM detector 34 for detecting the amount of PM. The other insulating substrate 33 is provided with a heater 35 for heating the sensor element 31. The sensor element 31 is a lamination structure in which two layers of the insulating substrates 32 and 33 are stacked with each other. The insulating substrate 32 corresponds to an attachment portion.

A pair of detection electrodes 36a and 36b are provided on the surface of the insulating substrate 32 opposite to the other insulating substrate 33, while being spaced apart from each other. The PM detector 34 is made of the pair of the detection electrodes 36a and 36b. Each of the detection electrodes 36a and 36b has a comb-like shape with teeth. The teeth of the combs of the detection electrodes 36a and 36b are alternatively arranged to be opposite to each other at predetermined intervals. The heater 35 includes a heating element made of, for example, an electrically-heated wire.

The shape of the pair of the detection electrodes 36a and 36b is not limited to the above-mentioned one, and may be a curved one. Alternatively, the detection electrodes 36a and 36b may be formed from a pair of electrode portions each of which is formed of one wire and which are arranged opposed to each other in parallel, while being spaced apart by a predetermined distance.

Although not shown, the PM sensor 17 includes a holder for holding the sensor element 31. The sensor element 31 is fixed to an exhaust pipe with its one end held by the holder. In this case, a part including at least the PM detector 34 and the heater 35 is positioned in the exhaust pipe, while the PM sensor 17 is attached to the exhaust pipe with the insulating substrate 32 (PM attachment portion) of the sensor element 31 directed toward the upstream side of the exhaust gas. Thus, when exhaust gas containing PM flows through the exhaust pipe, the PM is attached and accumulated onto the detection electrodes 36a and 36b and its surroundings over the insulating substrate 32. The PM sensor 17 has a protective cover for covering protrusion parts of the sensor element 31.

When PM in the exhaust gas is attached and accumulated onto the insulating substrate 32 of the sensor element 31, the PM sensor 17 with the above structure detects the amount of PM using a change in resistance of the PM detector 34 (that is, resistance between the pair of detection electrodes 36a and 36b) which correspond to the amount of accumulated PM.

As shown in FIG. 3, the PM sensor 17 has the following electric configuration. That is, the PM detector 34 of the PM sensor 17 has one end thereof connected to a sensor power supply 41, and the other end thereof connected to a shunt resistor 42. The sensor power supply 41 is constructed of, for example, a constant-voltage circuit. The constant voltage Vcc is 5 V, for example. In this case, the PM detector 34 and the shunt resistor 42 form a voltage-dividing circuit 40, in which a voltage of an intermediate point is input as a PM detection voltage Vpm (sensor detection value) to the ECU 20. That is, in the PM detector 34, the resistance Rpm changes according to the amount of accumulated PM. The PM detection voltage Vpm is changed by the resistance Rpm and the resistance Rs of the shunt resistor 42. Then, the PM detection voltage Vpm is input to a microcomputer 44 via an A/D converter 43.

When Vcc=5 V, when and Rs=5 kΩ, the PM detection voltage Vpm can be determined by the following formula (1):

$$Vpm = 5\ V \times 5\ k\Omega / (5\ k\Omega + Rpm) \quad (1)$$

At this time, when the amount of accumulated PM is 0 (or about 0), the resistance Rpm of the PM detector 34 becomes infinite, thereby resulting in Vpm=0 V. When the resistance Rpm of the PM detector 34 decreases, for example, decreases to 1 kΩ due to the accumulation of PM, the PM detection voltage Vpm becomes in Vpm=4.16V. In this way, the PM detection voltage Vpm changes according to the amount of accumulated PM at the PM detector 34. The microcomputer 44 calculates the amount of accumulated PM according to the PM detection voltage Vpm.

The voltage-dividing circuit 40 forms the signal output circuit. The PM detection voltage Vpm is variably changed by the voltage-dividing circuit 40 in an output range of 0 to 5 V. In this case, the output upper limit of the PM detection voltage Vpm is about 5 V, and strictly, slightly lower than 5 V, namely, 4.95V.

In this embodiment, particularly, when the PM is accumulated over the PM detector 34 as mentioned above, for example, when the resistance Rpm of the PM detector 34 becomes 1 kΩ, the PM detection voltage Vpm is "4.16 V", which is small as compared to the output upper limit (5V) of the PM detection voltage Vpm. This is because an increase in the PM detection voltage Vpm is taken into consideration during the forcible burning of the PM. The details thereof will be described later. The range of change in the PM detection voltage Vpm during the PM forcible burning is 4.16 to 5 V.

The heater 35 of the PM sensor 17 is connected to a heater power supply 45. The heater power supply 45 is, for example, a vehicle-mounted battery. The heater 35 is heated by power supplied from the vehicle-mounted battery. In this case, a transistor 46 is connected as a switching element to the lower side of the heater 35. The heating operation of the heater 35 is controlled by turning on/off the transistor 46 via the microcomputer 44.

When the energization of the heater 35 is started with the PM accumulated on the insulating substrate 32, the temperature of the accumulated PM increases, thereby forcedly burning the accumulated PM. Such forcible burning of the PM burns and removes the PM accumulated on the insulating substrate 32. For example, at the start of the engine, at the end of the operation of the engine, or when the amount of accumulated PM is determined to reach a predetermined amount, the microcomputer 44 determines that a request for forcible burning of the PM is made, and thus controls the heating operation of the heater 35.

Further, the ECU 20 is provided with an EEPROM 47 serving as a memory for a backup to store therein various types of studied values, abnormality diagnosis values (diagnostic data, or diagdata) or the like.

In the present embodiment, the diagnosis of abnormality of the PM sensor 17 is performed based on a variation of the PM detection voltage Vpm when removing the PM accumulated on the PM sensor 17 by the forcible burning. Now, the abnormality diagnosis processes will be described below in more detail. First, a basic operation during the PM forcible burning will be described below using the time chart shown in FIG. 4.

Figure 4:
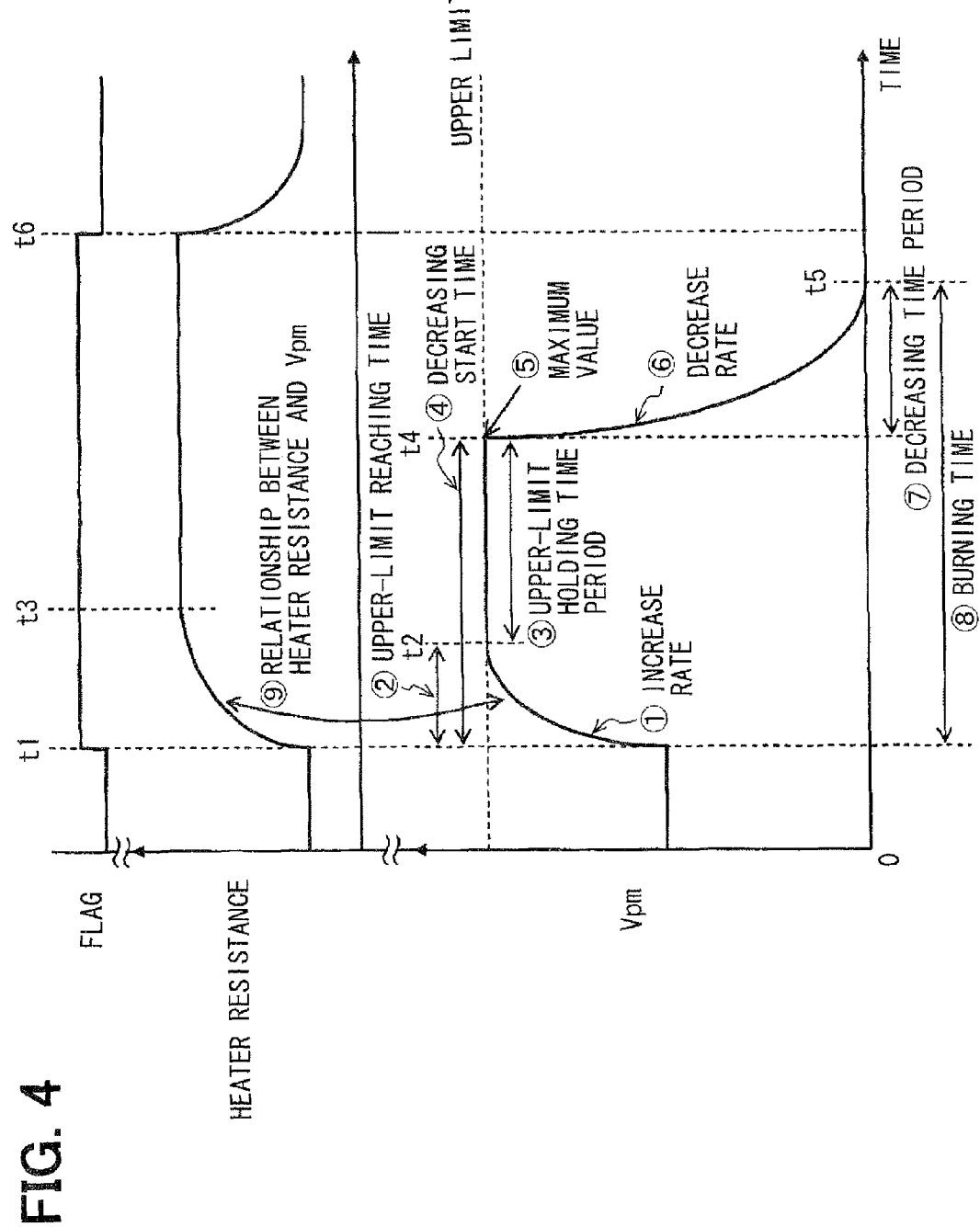
FIG. 4 is a time chart for explaining a basic operation in a PM forcible burning.

Referring to FIG. 4, at the timing t1, a PM burning requirement flag is set to start the energization of the heater 35 of the PM sensor 17, so as to increase a heater resistance. During the period from the timing t1 to the timing t2, the temperature of the accumulated PM on the PM sensor 17 (insulating substrate 32) increases so as to decrease the resistance between the electrodes, thereby increasing the PM detection voltage Vpm. That is, the PM has the temperature property that the resistance decreases with the increased temperature. When the resistance decreases, the PM detection voltage Vpm increases and reaches to the output upper limit, which is then kept.

The PM detection voltage Vpm reaches the output upper limit (for example, 4.95 V) at the timing t2, and thereafter holds the output upper limit. The heater resistance gradually increases after the start of energization of the heater, and then reaches and holds the upper limit of the heater resistance at timing t3. The heater resistance upper limit is a resistance at which the increase in temperature of the heater 35 converges to a constant.

During the period from the timing t2 to the timing t4, the PM detection voltage Vpm reaches and holds the output upper limit. Further, during the period from the timing t2 to the timing t4, the burning of the accumulated PM is started with the increased temperature of the accumulated PM. The PM located at the PM detector 34 is gradually removed by the burning of the accumulated PM. When the resistance between the electrodes begins to increase together with the burning, the PM detection voltage Vpm also begins to decrease from the output upper limit at the timing t4 together with the increase in resistance between the electrodes.

Thereafter, at the timing t5, all the PM on the insulating substrate 32 is burned and removed. The state of continuity between the electrodes through the PM is eliminated, and thereby the PM detection voltage Vpm returns to 0 V (0 point) which is the output lower limit. At the timing t6, the heater is turned off because of the end of a series of forcible burning processes, and the PM burning requirement flag is reset.

In this embodiment, taking into consideration that the above behavior appears during the PM forcible burning, a plurality of abnormality diagnosis parameters are set based on the PM detection voltage Vpm during the PM forcible burning. The diagnosis of the abnormality of the PM sensor 17 is carried out based on the abnormality diagnosis parameters. In the following, the outline of the respective abnormality diagnosis parameters, and first to ninth abnormality diagnosis processes performed based on the parameters will be described. For convenience of explanation, FIG. 4 indicates the abnormality diagnosis parameters set in this embodiment by ① to ⑨.

First Abnormality Diagnosis Process (See ① in FIG. 4)

In a first abnormality diagnosis process, the rate of increase in the PM detection voltage Vpm directly after the start of energization of the heater 35 is set as an abnormality diagnosis parameter. That is, the rate of increase in the PM detection voltage Vpm during the period from the timing t1 to the timing t2 shown in FIG. 4 is calculated. By comparing the calculated increasing rate with a predetermined rate of increase in a normal state, the diagnosis of abnormality of the PM sensor 17 is carried out. The rate of increase is calculated as an average rate. Alternatively, an acceleration of increase (gradient indicative of a change in increasing rate) is calculated, and the calculated value can be set as the parameter.

Second Abnormality Diagnosis Process (See ② in FIG. 4)

In a second abnormality diagnosis process, an upper limit reaching time specifically, the time until the PM detection voltage Vpm reaches the output upper limit directly after the start of energization of the heater 35 is set as the abnormality diagnosis parameter. The upper limit reaching time shown by ② in FIG. 4 is calculated as the period of time required for the PM detection voltage Vpm to reach the output upper limit after the start of energization of the heater until the voltage Vpm reaches the output upper limit. That is, the period of time required from the timing t1 to the timing t2 shown in FIG. 4 is calculated. By comparing the calculated period of time required with a predetermined period of time in the normal state, the diagnosis of abnormality of the PM sensor 17 is carried out.

Third Abnormality Diagnosis Process (See ③ in FIG. 4)

In a third abnormality diagnosis process, an upper-limit holding time period, specifically, the time period during which the PM detection voltage Vpm holds the output upper limit in the state of energization of the heater 35, is set as the abnormality diagnosis parameter. That is, an elapsed time from the timing t2 to the timing t4 shown in FIG. 4 is calculated. By comparing the calculated elapsed time with a predetermined time period during which the upper limit is held at the normal state, the diagnosis of the abnormality of the PM sensor 17 is carried out.

Fourth Abnormality Diagnosis Process (See ④ in FIG. 4)

In a fourth abnormality diagnosis process, a decreasing start time, specifically, the time at which the PM detection voltage Vpm begins to decrease with the actual start of burning the PM in the state of energization of the heater 35 is set as the abnormality diagnosis parameter. That is, an elapsed time from the timing t1 to the timing t4 shown in FIG. 4 is calculated. By comparing the calculated elapsed time with the predetermined decreasing start time in the normal state (period of time required for the voltage to begin to decrease), the diagnosis of abnormality of the PM sensor 17 is carried out.

Fifth Abnormality Diagnosis Process (See ⑤ in FIG. 4)

In a fifth abnormality diagnosis process, the maximum value of the PM detection voltage Vpm detected in the state of energization of the heater 35 is set as the abnormality diagnosis parameter. That is, during the period from the timing t1 to the timing t4 shown in FIG. 4, the PM detection voltage Vpm is to reach the output upper limit. Thus, the maximum value of the PM detection voltage Vpm during the period of time from the timing t1 to the timing t4 is calculated. By comparing the calculated maximum Vpm with a predetermined maximum value (output upper limit) in the normal state, the diagnosis of abnormality of the PM sensor 17 is carried out.

Sixth Abnormality Diagnosis Process (See ⑥ in FIG. 4)

In a sixth abnormality diagnosis process, the rate of decrease in the PM detection voltage Vpm after the actual start of burning the PM is set as an abnormality diagnosis parameter. That is, the rate of decrease in the PM detection voltage Vpm during the period from the timing t4 to the timing t5 shown in FIG. 4 is calculated. By comparing the calculated decreasing rate with a predetermined rate of decrease in the normal state, the diagnosis of abnormality of the PM sensor 17 is carried out. The decreasing rate is calculated as an average velocity. Additionally, or alternatively, a decreasing acceleration (inclination of change in decreasing rate) can be calculated, and thus can be used as a parameter.

Seventh Abnormality Diagnosis Process (See ⑦ in FIG. 4)

In a seventh abnormality diagnosis process, a decreasing time period, specifically, the period of time required from when the PM detection voltage Vpm begins to decrease after the actual start of burning the PM until when the voltage Vpm reaches the output lower limit (0 V) is set as the abnormality diagnosis parameter. That is, the time period required for the voltage Vpm to decrease from the timing t4 to the timing t5 shown in FIG. 4 is calculated. By comparing the calculated decreasing time period with a predetermined decreasing time period in the normal state, the diagnosis of abnormality of the PM sensor 17 is carried out.

Eighth Abnormality Diagnosis Process (See ⑧ in FIG. 4)

In an eighth abnormality diagnosis process, a burning time period, specifically, the period of time required, from when the PM detection voltage Vpm increases after the start of energization of the heater 35, until when the voltage Vpm decrease to reach the output lower limit (0 V), is set as the abnormality diagnosis parameter. That is, the burning time period required from the timing t1 to the timing t5 shown in FIG. 4 is calculated. By comparing the calculated burning time period with a predetermined burning time period in the normal state, the diagnosis of abnormality of the PM sensor 17 is carried out.

Ninth Abnormality Diagnosis Process (See ⑨ in FIG. 4)

In a ninth abnormality diagnosis process, the relationship between the change of increase in the PM detection voltage Vpm and the change of increase in the heater resistance directly after the start of energization of the heater 35 is set as the abnormality diagnosis parameter. That is, the rate of increase in the PM detection voltage Vpm and the rate of increase in the heater resistance during the time period from the timing t1 to the timing t3 are calculated. By comparing the ratio between both the calculated increase rates with a predetermined ratio between both increasing rates in the normal state, the diagnosis of abnormality of the PM sensor 17 is carried out.

Now, the specific steps of the above first to ninth abnormality diagnosis processes will be described below with reference to the flowcharts shown in FIGS. 5 to 9. The procedure shown in each flowchart is repeatedly performed at predetermined intervals by the microcomputer 44.

Figure 5:
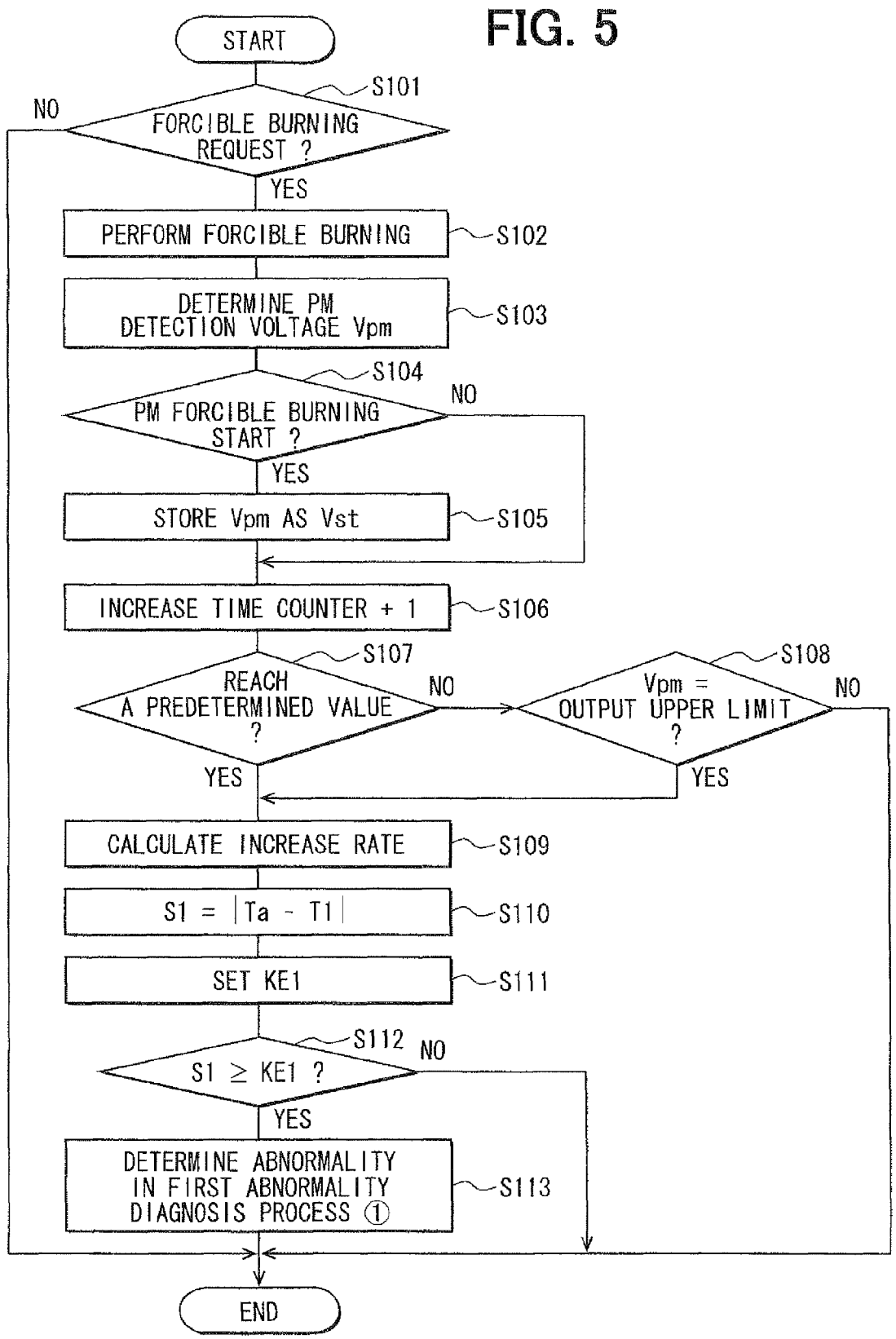
FIG. 5 is a flowchart showing a first abnormality diagnosis process.

First, the first abnormality diagnosis process will be described below based on the flowchart shown in FIG. 5, Referring to FIG. 5, in step S101, it is determined whether or not a request for performing the forcible burning is made at the PM sensor 17. In this embodiment, a PM burning requirement flag is set by at lease one of the start time of operation of the engine, the end time of operation of the engine, a time where the amount of accumulated PM reaches a predetermined amount, and a time period of operation of the engine or a time where vehicle traveling distance after the previous PM forcible burning process reaches a predetermined value, so that the forcible burning requirement is made. When no forcible burning requirement is determined to be made, the present process is ended as it is. When the PM forcible burning process is being performed while no forcible burning requirement is determined, the forcible burning process is immediately ended.

When the request for the forcible burning is determined to be made, the operation proceeds to the following step S102 so as to perform the PM forcible burning process and the abnormality diagnosis process of the PM sensor 17. In step S102, the PM forcible burning process is performed. Specifically, the energization of the heater 35 for the PM sensor 17 is turned on. In step S103, the present PM detection voltage Vpm is determined. In next step S104, it is determined whether or not the present process is the first process after the start of the PM forcible burning. If YES, the operation proceeds to step S105 in which the present PM detection voltage Vpm is stored as a burning start voltage Vst.

Thereafter, in step S106, an increase time counter is increased by 1. The increase time counter is a counter for measuring an elapsed time from the start of energization of the heater 35 as a starting point.

Thereafter, in step S107, it is determined whether or not the increase time counter reaches a predetermined value. If NO in step S107, it is determined whether or not the present PM detection voltage Vpm reaches or holds the output upper limit in step S108. If YES in either step S107 or step S108, the operation proceeds to the following step S109 in which the rate of increase in the PM detection voltage Vpm is calculated. At this time, a difference between the present PM detection voltage Vpm and the burning start voltage Vst is divided by the value of the increase time counter, thereby calculating the average rate at the time of increase in the PM detection voltage Vpm as the "increasing rate".

In step S110, a diagnosis value S1 is calculated based on the increasing rate calculated in step S109. In the present embodiment, the diagnosis value S1 is calculated as a difference between the actual increasing rate Ta (calculated value in step S109) and a standard increasing rate T1 in the normal state. At this time, the actual increasing rate Ta changes according to the burning start voltage Vst (that is, amount of accumulated PM). The higher the burning start voltage Vst, the more the increasing rate (average increasing rate). Based on the burning start voltage Vst, a reference rate T1 is calculated as the standard increasing rate. An absolute value of the difference between the actual increasing rate Ta and the reference rate T1 is set as the diagnosis value S1 (S1=|Ta−T1|).

Thereafter, in step S111, an abnormality determination value KE1 is set. The abnormality determination value KE1 is defined based on an allowable level of a deviation of increasing rate (difference in rate). It is noted that the abnormality determination value KE1 can be set by correction using the burning start voltage Vst. In step S112, it is determined whether or not the diagnosis value S1 is equal to or more than the abnormality determination value KE1. When S1≥KE1, the operation proceeds to step S113 in which it is determined that the abnormality is caused in the PM sensor 17. When the abnormality of the PM sensor is determined to be caused, abnormality diagnosis data is stored in the EEPROM 47 or the like. Alternatively or additionally, each of an upper limit and a lower limit of a normal range can be set as the abnormality determination value, and it can be determined whether or not the diagnosis value S1 is in the normal range.

Figure 6:
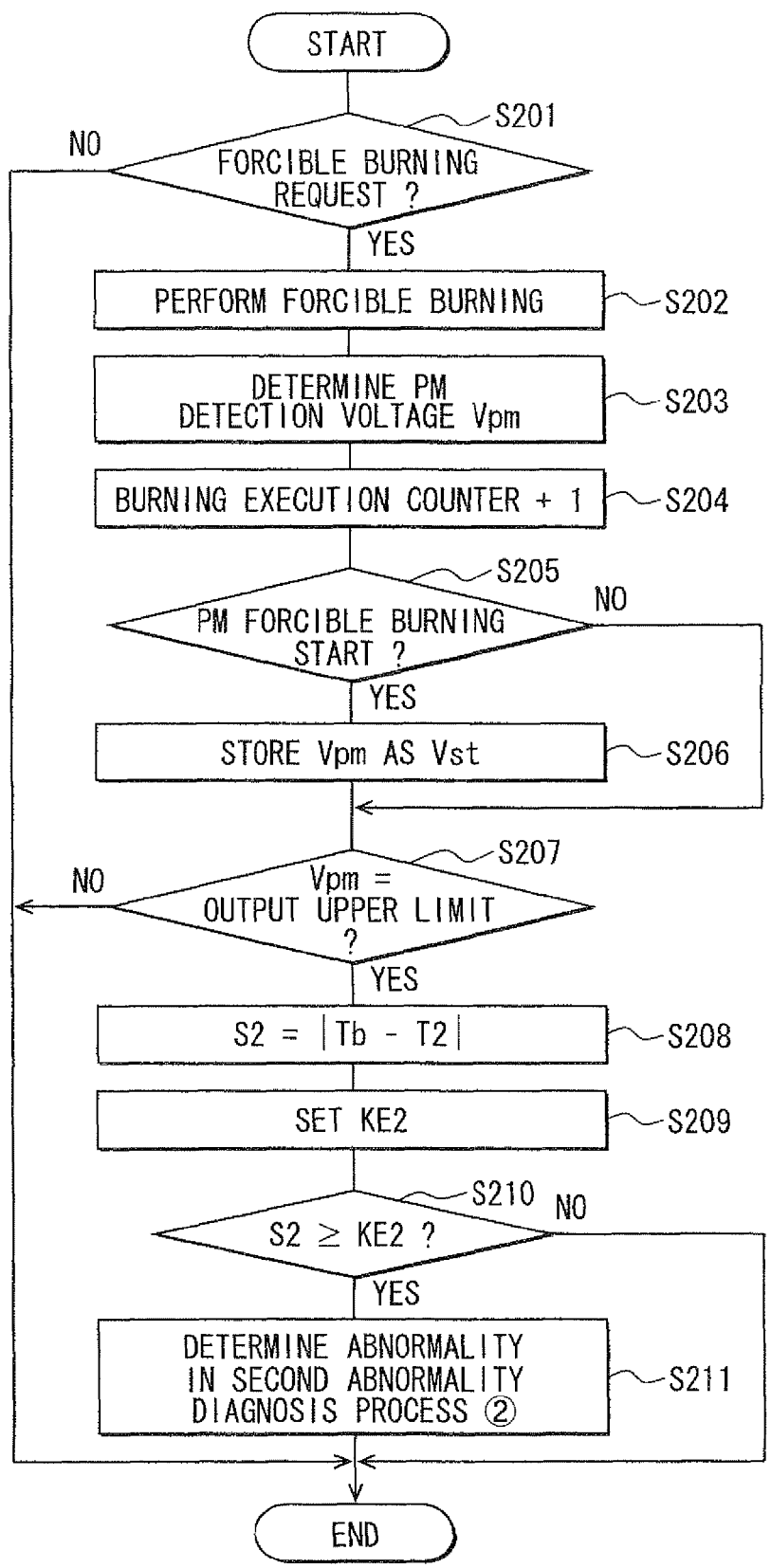
FIG. 6 is a flowchart showing a second abnormality diagnosis process.

Next, the second abnormality diagnosis process will be described below based on the flowchart shown in FIG. 6. Referring to FIG. 6, in step S201, it is determined whether or not a request for the forcible burning is made at the PM sensor 17. If Yes, the operation proceeds to the following step S202 in which the PM forcible burning process is performed (with the heater energized). In step S203, the present PM detection voltage Vpm is determined. Steps S201 to S203 have the same processes as those in the steps S101 to S103 shown in FIG. 5.

Thereafter, in step S204, a burning execution counter is incremented by 1. In next step S205, it is determined whether or not the present process is the first process after the start of the PM forcible burning. If YES, the operation proceeds to step S206 in which the present PM detection voltage Vpm is stored as a burning start voltage Vst.

Then, in step S207, it is determined whether or not the present PM detection voltage Vpm reaches the output upper limit. If YES in step S207, the operation proceeds to the following step S208 in which a diagnosis value S2 regarding the upper limit reaching time is calculated based on a value of the burning execution counter at the timing when the PM detection voltage Vpm gets to (reaches) the output upper limit. In this embodiment, the diagnosis value S2 is calculated as a difference between the actual upper limit reaching time (counter value) and a standard reaching time in the normal state. At this time, the upper limit reaching time changes according to the burning start voltage Vst (that is, the amount of accumulated PM). The higher the burning start voltage Vst, the shorter the period of time required for the PM detection voltage to reach the upper limit. A reference time T2 is calculated as the standard reaching time based on the burning start voltage Vst. An absolute value of the difference between the value of the burning execution counter Tb and the reference time T2 is set as the diagnosis value S2 (S2=|Tb−T2|).

Then, in step S209, an abnormality determination value KE2 is set. The abnormality determination value KE2 is defined based on an allowable level of a deviation from the upper limit reaching time. The abnormality determination value KE2 can be set by correction using the burning start voltage Vst. In step S210, it is determined whether or not the diagnosis value S2 is equal to or more than the abnormality determination value KE2. When S2≥KE2, the control operation proceeds to step S211 in which it is determined that the abnormality is caused in the PM sensor 17. When the abnormality of the PM sensor 17 is determined to be caused, abnormality diagnosis data is stored in the EEPROM 47 or the like. Alternatively or additionally, each of an upper limit and a lower limit of a normal range can be set as the abnormality determination value KE2, and it can be determined whether or not the diagnosis value S2 is in the normal range by using the abnormality determination value KE2.

Figure 7:
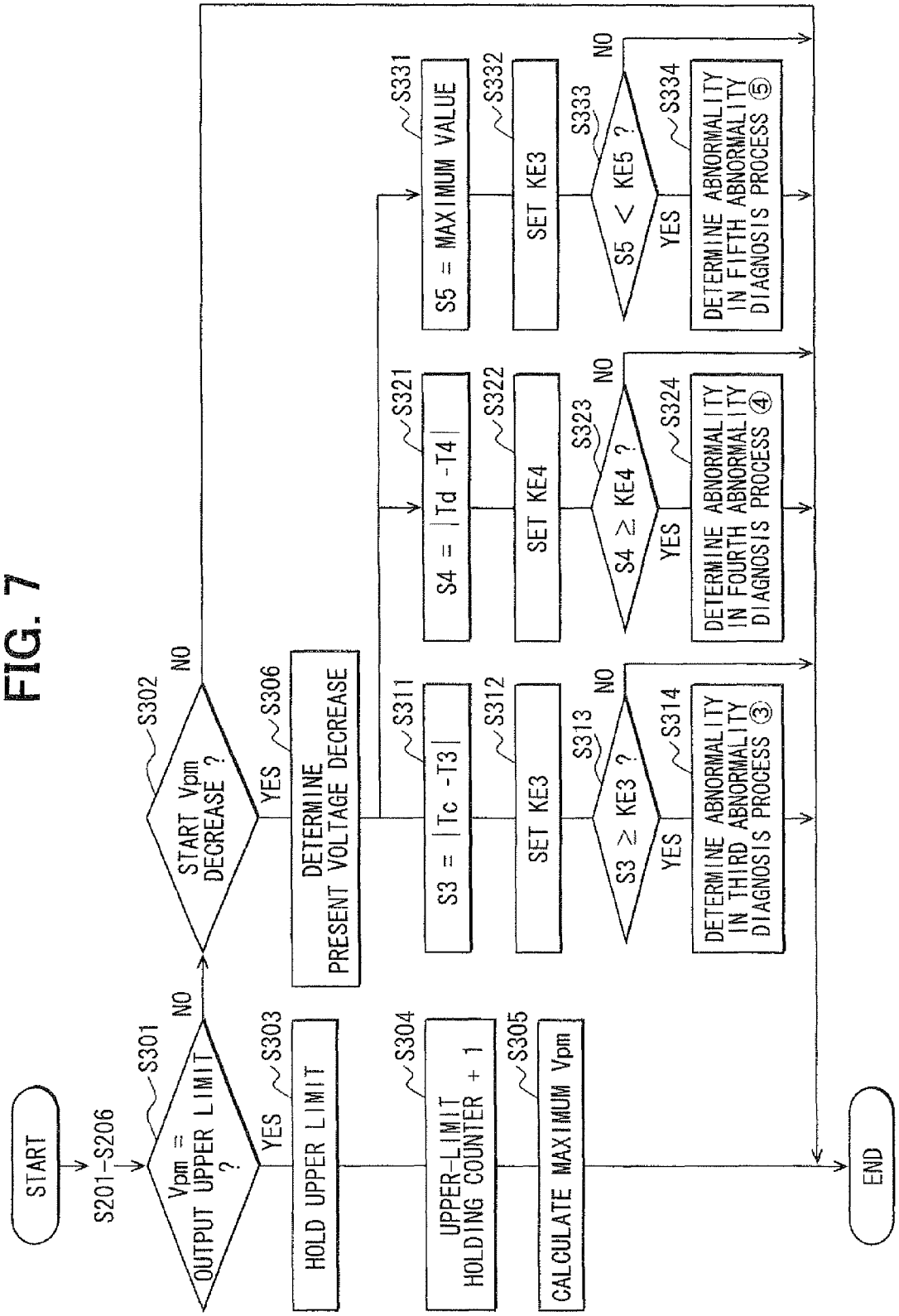
FIG. 7 is a flowchart showing third to fifth abnormality diagnosis processes.

Next, the third to fifth abnormality diagnosis processes will be described below based on the flowchart of FIG. 7. FIG. 7 omits the explanation of the steps S201 to S206 which are the same as the steps S201 to S206 shown in FIG. 6. After performing the steps S201 to S206, the control operation proceeds to step S301.

In step S301, it is determined whether or not the present PM detection voltage Vpm reaches the output upper limit. If NO in step S301, it is determined whether or not the PM detection voltage Vpm begins to decrease from the state of reaching the upper limit in step S302. Referring to FIG. 4, during the period from the timing t1 to the timing t2, the determination is "NO" in each of the steps S301 and S302, and the present process is temporarily ended. During the period from the timing t2 to the timing t4, the determination is "YES" in step S301, and then the control operation proceeds to step S303. At the timing t4, the determination is "NO" in step S301, and the determination of "YES" is made in step S302. Then, the control operation proceeds to step S306.

When the control operation proceeds to step S303, the present PM detection voltage Vpm is determined to be in the state of holding the upper limit in step S303. In the following step S304, the upper-limit holding counter is increased by 1. In step S305, the maximum value of the PM detection voltage Vpm is calculated while the PM detection voltage holds the upper limit. Specifically, during the upper limit holding time period (from the timing t2 to the timing t4 shown in FIG. 4), every time the PM detection voltage Vpm is determined, a larger one of the previous maximum voltages and the determined voltage Vpm is stored as a maximum value by comparing with the previous maximum voltages.

In contrast, when the operation proceeds to step S306, the present voltage is determined to be decreased in step S306, and then the following abnormality diagnosis process is performed. FIG. 7 totally illustrates the third, fourth, and fifth abnormality diagnosis processes. Steps S311 to S314 correspond to the third abnormality diagnosis process, steps S321 to S324 correspond to the fourth abnormality diagnosis process, and steps S331 to S334 correspond to the fifth abnormality diagnosis process.

First, in the third abnormality diagnosis process, in step S311, the diagnosis value S3 regarding the upper limit holding time period is calculated based on the value of the upper limit reaching counter at a time where the PM detection voltage Vpm begins to decrease (i.e., at the time of end of holding the upper limit). in this embodiment, the diagnosis value S3 is calculated as a difference between the actual upper limit holding time period (counter value) and a standard holding time period in the normal state. At this time, the upper-limit holding time period changes according to the burning start voltage Vst (that is, the amount of accumulated PM). The higher the burning start voltage Vst, the longer the upper-limit holding time period. A reference time T3 is calculated as the standard holding time period based on the burning start voltage Vst. An absolute value between the reference time T3 and the upper limit counter value Tc is set as the diagnosis value S3 (S3=|Tc−T3|).

Then, in step S312, an abnormality determination value KE3 is set. The abnormality determination value KE3 is defined based on an allowable level of a deviation of the upper limit holding time period. The abnormality determination value KE3 can be set by correction using the burning start voltage Vst. In step S313, it is determined whether or not the diagnosis value S3 is equal to or more than the abnormality determination value KE3. If S3≥KE3, the control operation proceeds to step S314 in which the abnormality is determined to be caused in the PM sensor 17. When the abnormality is determined to be caused, abnormality diagnosis data is stored in the EEPROM 47 or the like.

In the fourth abnormality diagnosis process, in step S321, a diagnosis value S4 regarding the decreasing start time is calculated based on a value of the burning execution counter Td at the time where the PM detection voltage Vpm begins to decrease (i.e., at the end of the time for holding the upper limit). In this embodiment, the diagnosis value S4 is calculated as a difference between the actual decreasing start time (counter value) and the standard decreasing start time in the normal state. At this time, the decreasing start time changes according to the burning start voltage Vst (that is, the amount of accumulated PM). The higher the burning start voltage Vst, the longer the period of time required up to the start of decreasing. Thus, the reference time T4 is calculated as the standard decreasing start time based on the burning start voltage Vst. An absolute value of the difference between the burning execution counter value Td and the reference time T4 is regarded as the diagnosis value S4 (S4=|Td−T4|).

Thereafter, in step S322, an abnormality determination value KE4 is set. The abnormality determination value KE4 is defined based on an allowable level of a deviation in decreasing start time. The abnormality determination value KE4 can be set by correction using the burning start voltage Vst. In step S323, it is determined whether or not the diagnosis value S4 is equal to or more than the abnormality determination value KE4. If S4≥KE4, the operation proceeds to step S324 in which the PM sensor 17 is determined to become abnormal. When the abnormality is determined to be caused, the abnormality diagnosis data is stored in an EEPROM 47 and the like.

An upper limit and a lower limit of the normal range can be set for each of the above abnormality determination values KE3 and KE4, and it can be determined whether or not the diagnosis value S3 or S4 is in the normal range.

In the fifth abnormality diagnosis process, the maximum value (calculated value in step S305) of the PM detection voltage Vpm calculated in step S331, while the upper limit is held, is calculated as a diagnosis value S5. Thereafter, in step S332, the abnormality diagnosis value KE5 is set. The abnormality diagnosis value KE5 is defined as the output upper limit (e.g., 4.95 V). In step S333, it is determined whether or not the diagnosis value S5 is less than the abnormality diagnosis value KE5. If S5<KE5, the control operation proceeds to step S334 in which the abnormality is caused in the PM sensor 17. When the abnormality is determined to be caused, the abnormality diagnosis data is stored in the EEPROM 47 or the like.

Figure 8:
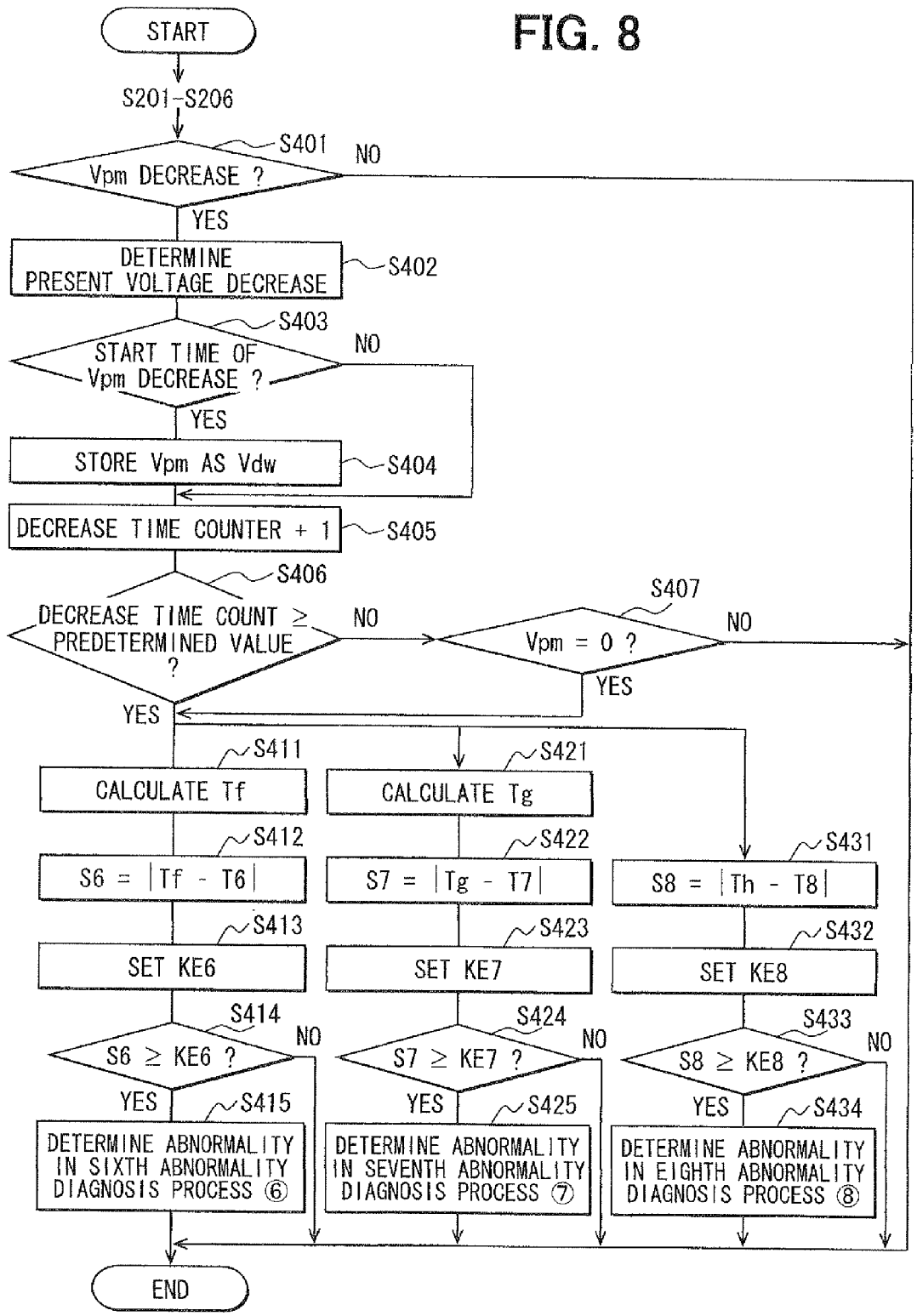
FIG. 8 is a flowchart showing sixth to eighth abnormality diagnosis processes.

Now, the sixth to eighth abnormality diagnosis processes will be described below based on the flowchart of FIG. 8. FIG. 8 omits the explanation of the steps S201 to S206 which are the same as those shown in FIG. 6. After performing the steps S201 to S206, the operation proceeds to step S401.

In step S401, it is determined whether or not the present PM detection voltage Vpm begins to decrease from the state of reaching the upper limit. Referring to FIG. 4, during the period from the timing t1 to the timing t4, the determination is NO in step S401, and the present process is temporarily ended. After the timing t4, the determination of YES is made in step S401, and the control operation proceeds to step S402.

The operation proceeds to step S402 in which the present PM detection voltage is determined to be decreased. In next step S403, it is determined whether or not the present process is the first process after the start of voltage drop. If YES, the control operation proceeds to step S404 in which the present PM detection voltage Vpm is stored as a decreasing start voltage Vdw.

Then, in step S405, a decrease time counter is incremented by 1. The decrease time counter is a counter for measuring an elapsed time from the start of decrease in the PM detection voltage Vpm using the starting time of decrease in the PM detection voltage Vpm as a starting point.

Thereafter, in step S406, it is determined whether or not the decrease time counter reaches a predetermined value. If NO in step S406, it is determined whether or not the present PM detection voltage Vpm reaches the output lower value (e.g., 0 V) in step S407. Steps S421 to 425 correspond to the seventh abnormality diagnosis process. If YES in any one of steps S406 and S407, the following abnormality diagnosis is performed. FIG. 8 totally shows the sixth, seventh, and eighth abnormality diagnosis processes. Steps S411 to S415 correspond to the sixth abnormality diagnosis process. Steps S421 to S425 correspond to the seventh abnormality diagnosis process. Steps S431 to 434 correspond to the eighth abnormality diagnosis process.

In the sixth abnormality diagnosis process, in step S411, a rate of decrease in the PM detection voltage Vpm is calculated. At this time, the decreasing start voltage Vdw is divided by the value of the decrease time counter, so that an average rate of decrease in the PM detection voltage Vpm is calculated as a "decreasing rate".

In step S412, a diagnosis value S6 is calculated based on the decreasing rate calculated in step S411. In this embodiment, the diagnosis value S6 can be calculated as a difference between the actual decreasing rate Tf (calculated value in step S411) and a standard decreasing rate T6 in the normal state. At this time, the decreasing rate changes according to the decreasing start voltage Vdw. The lower the decreasing start voltage Vdw, the smaller the decreasing rate (average decreasing rate). The reference rate T6 is calculated as the normal decreasing rate based on the decreasing start voltage Vdw. An absolute value of the difference between the actual decreasing rate Tf and the reference rate T6 is set as the diagnosis value S6 (S6=|Tf−T6|). The reference rate T6 can be calculated based on the burning start voltage Vst.

Thereafter, in step S413, an abnormality determination value KE6 is set. The abnormality determination value KE6 is defined based on an allowable level of a deviation of decreasing rate (rate difference). The abnormality determination value KE6 can be set by correction using the decreasing start voltage Vdw or the burning start voltage Vst. In step S414, it is determined whether or not the diagnosis value S6 is equal to or more than the abnormality determination value KE6. If S6≥KE6, the control operation proceeds to step S415 in which it is determined that the abnormality is caused in the PM sensor 17. When the abnormality is determined to be caused, the abnormality diagnosis data is stored in the EEPROM 47 or the like.

In the seventh abnormality diagnosis process, in step S421, a diagnosis value S7 regarding the decreasing time period Tg is calculated based on the value of the decrease time counter at the time where the PM detection voltage Vpm holds (reaches) 0V in step S421. In this embodiment, the diagnosis value S7 is calculated as a difference between the actual decreasing time period Tg (counter value) and a standard decreasing time period T7 in the normal state. At this time, the decreasing time period Tg changes according to the decreasing start voltage Vdw. The lower the decreasing start voltage Vdw, the shorter the decrease time period Tg. A reference time T7 as the standard decreasing time period is calculated based on the decreasing start voltage Vdw. A diagnosis value S7 is set as an absolute of a difference between the value of the decrease time period Tg and the reference time T7 (S7=|Tg−T7|). The reference time T7 can be calculated based on the burning start voltage Vst.

Thereafter, in step S423, an abnormality determination value KE7 is set. The abnormality determination value KE7 is defined based on an allowable level of a deviation in the decreasing time period. The abnormality determination value KE7 can be set by correction using decreasing start voltage Vdw or burning start voltage Vst. In step S424, it is determined whether or not the diagnosis value S7 is equal to or more than the abnormality determination value KE7. If S7≥KE7, the control operation proceeds to step S425 in which the abnormality is determined to be caused in the PM sensor 17. When the abnormality is determined to be caused, the abnormality diagnosis data is stored in the EEPROM 47 or the like.

In the eighth abnormality diagnosis process, in step S431, a diagnosis value S8 regarding a burning time period is calculated based on a burning execution counter at the time where the PM detection voltage Vpm holds (reaches) 0 V. In this embodiment, the diagnosis value S8 is calculated as a difference between an actual burning time period Th (counter value) and a standard burning time period T8 in the normal state. At this time, the burning time period changes according to the burning start voltage Vst (see step S105 in FIG. 5). The higher the burning start voltage Vst is, the longer the burning time period is. A reference time T8 as the standard burning time period is calculated based on the burning start voltage Vst. An absolute value of the difference between the burning execution counter Th and the reference time period T8 is set as a diagnosis value S8 (S8=|Th−T8|).

Thereafter, in step S432, an abnormality determination value KE8 is set. The abnormality determination value KE8 is defined based on an allowable level of a deviation in the burning time period. The abnormality determination value KE8 can be set by correction using the burning start voltage Vst. In step S433, it is determined whether or not the diagnosis value S8 is equal to or more than the abnormality determination value KE8. If S8≥KE8, the control operation proceeds to step S434 in which the abnormality is determined to be caused in the PM sensor 17. When the abnormality is determined to be caused, the abnormality diagnosis data is stored in the EEPROM 47 or the like.

An upper limit and a lower limit of a normal range can be set for each of the abnormality determination values KE6 to KE8 as described above, and it can be determined whether or not one of the diagnosis values S6 to S8 is in the normal range.

Next, a ninth abnormality diagnosis process will be described below based on the flowchart shown in FIG. 9. Referring to FIG. 9, in step S501, it is determined whether or not a request for the forcible burning is made at the PM sensor 17. If YES, the control operation proceeds to step S502 in which the PM forcible burning process is carried out (with the heater energized). In step S503, the present PM detection voltage Vpm is determined. Steps S501 to S503 have the same processes respectively as in steps S101 to S103 shown in FIG. 5. Therefore, the explanation of steps S501 to S503 is omitted.

Thereafter, in step S504, a present heater resistance is determined. The heater resistance is calculated by a heater resistance calculating means provided in the ECU 20. Specifically, a heater application voltage (battery voltage) and a heater current are detected in energization of the heater, and then the heater resistance is calculated based on the detected values.

In the following step S505, it is determined whether or not the present process is the first process after the start of the PM forcible burning. If YES, the control operation proceeds to step S506 in which the present PM detection voltage Vpm is stored as a burning start voltage Vst. In step S507, the present heater resistance is stored as a heater resistance Rst at the start of burning.

Thereafter, in step S508, an increase time counter is increased by 1. The increase time counter is a counter for measuring an elapsed time from the start of energization of the heater as a starting point. Thereafter, in step S509, it is determined whether or not the increase time counter reaches a predetermined value. If NO in step S509, it is determined whether or not the present PM detection voltage Vpm reaches the output upper limit in step S510. Further, if NO in step S510, it is determined whether or not the heater resistance reaches the upper limit in step S511.

If YES in any of steps S509 to S511, the control operation proceeds to the following step S512 in which the rate of increase in the PM detection voltage Vpm is calculated. At this time, a difference between the present PM detection voltage Vpm and the burning start voltage Vst is divided by the value of the increase time counter, whereby the average rate of increase in the PM detection voltage Vpm is calculated as "increasing rate of detected voltage". In step S513, the rate of increase in the heater resistance is calculated. At this time, a difference between the present heater resistance and the heater resistance Rst at the start of burning is divided by the value of the increase time counter, whereby the average rate of increase in the heater resistance is calculated as "increasing rate of heater resistance".

In step S514, a diagnosis value S9 is calculated based on the detection voltage increasing rate calculated in step S512 and the heater resistance increasing rate calculated in step S513. At this time, the diagnosis value S9 is set as a ratio which is obtained by dividing the detection voltage increasing rate by the heater resistance increasing rate (S9=detection voltage increasing rate/heater resistance increasing rate).

Thereafter, in step S515, an abnormality determination value KE9 is set. The abnormality determination value KE9 is determined based on a standard ratio between both rates in the normal state. The abnormality determination value KE9 can be set by correction using the burning start voltage Vst with respect to the standard rate ratio in the normal state. In step S516, it is determined whether or not the diagnosis value S9 is equal to or more than the abnormality determination value KE9. If S9≥KE9, the control operation proceeds to step S517 in which the abnormality is determined to be caused in the PM sensor 17. When the abnormality is determined to be caused, the abnormality diagnosis data is stored in the EEPROM 47 or the like.

Figure 10A:
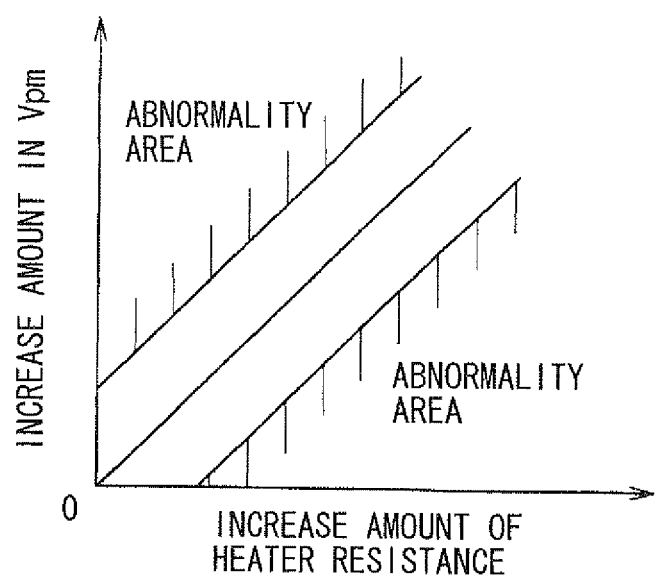
FIGS. 10A and 10B are diagrams showing a criterion of determination of abnormality used when performing the diagnosis of abnormality based on the relationship between the change in increase of PM detection voltage, and the change in increase of heater resistance.
Figure 10B:
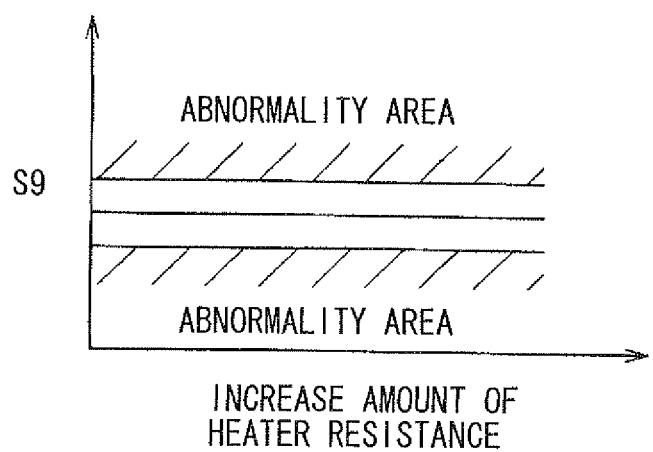

The criterion of determination of abnormality for performing the diagnosis of abnormality may be set based on the relationship between the change of increase in the PM detection voltage Vpm and the change of increase in the heater resistance as shown in FIGS. 10A and 10B. FIG. 10A illustrates abnormality determination zones in the relationship between an increase amount in the PM detection voltage Vpm (difference between the present PM detection voltage Vpm and the burning start voltage Vst) and an increase amount in the heater resistance (difference between the present heater resistance and the heater resistance Rst at the start of burning).

FIG. 10B illustrates abnormality determination zones in the relationship between the diagnosis value S9 and the increase amount in the heater resistance. The diagnosis value is a ratio between the rates calculated from the amount of increase in the PM detection voltage Vpm (difference between the present PM detection voltage Vpm and the burning start voltage Vst) and the amount of increase in the heater resistance (difference between the present heater resistance and the heater resistance Rst at the start of burning).

In the above embodiment described in detail, the PM detection voltage Vpm is determined while the accumulated PM at the PM detector 34 is heated by the heater 35, and the diagnosis of abnormality of the PM sensor 17 is performed based on the determined PM detection voltage Vpm. In this case, it is possible to previously recognize how the PM detection voltage Vpm changes in the normal state of the sensor at the time of energization of the heater (at the time of heating the heater). The presence or absence of the abnormality of the sensor 17 can be diagnosed by comparing the actual present PM detection voltage Vpm with a reference value of the PM detection voltage Vpm in the normal state. As a result, the abnormality of the PM sensor 17 can be suitably detected.

In the abnormality diagnosis process of this embodiment, the diagnosis of abnormality is carried out based on the behavior of the PM detection voltage Vpm in each of a period of time for increasing the PM detection voltage Vpm due to the temperature property of the PM, a period of time while the PM detection voltage Vpm holds the upper limit, and a period of time for decreasing the PM detection voltage Vpm due to the burning out of the PM. Thus, the diagnosis of abnormality can be minutely performed taking into consideration the change in the PM detection voltage Vpm in each period of time.

In the forcible burning of PM, the PM detection voltage Vpm at the start of burning (at the start of energization of the heater) is determined. At least one of the abnormality diagnosis parameter and the abnormality determination value is corrected based on the determined PM detection voltage Vpm. Thus, even if the PM detection voltage Vpm (amount of accumulated PM) at the start of energization of the heater becomes different in each case, fluctuations in abnormality diagnosis parameter and abnormality determination value depending on the PM detection voltage Vpm can be eliminated, thereby improving the accuracy of the abnormality diagnosis.

Other Embodiments

The present invention is not limited to the contents disclosed in the above embodiment, and may be applied as follows.

It is possible to change which one of the above first to ninth abnormality diagnosis processes is performed. At least one of the abnormality diagnosis processes may be performed in the above-described embodiment. Further, in each of the abnormality diagnosis processes described above, the cycle or timing of execution of the process may be individually set, and the respective abnormality diagnosis processes may be performed at different timings.

In the above embodiment, the voltage-dividing circuit 40 shown in FIG. 3 is used as the signal output circuit. This may be modified. For example, connection between the PM detector 34 and the shunt resistor 42 forming the voltage-dividing circuit may be reversed. Specifically, the PM detector 34 may be provided on the lower side, and the shunt resistor 42 may be provided on the higher side. In this arrangement, the PM detection voltage Vpm is determined by the following formula (2)

$$Vpm=5 \ V \times Rpm/(Rs+Rpm) \tag{2}$$

in which Rpm is a resistance of the PM detector 34, and Rs is a resistance (for example, 5 kΩ) of the shunt resistor 42.

In such a case, when the amount of accumulated PM is 0 (or about 0), the Vpm is 5 V (Vpm=5V). The value of 5 V corresponds to the origin (0 point). When the resistance Rpm of the PM detector 34 decreases to, for example, 1 kΩ due to the accumulation of PM, the Vpm is 0.83 V (Vpm=0.83V). The range of a voltage of the voltage-dividing circuit 40 is 0 to 5 V. The range of change in the PM detection voltage Vpm during the PM forcible burning is 0 to 0.83 V.

In the ninth abnormality diagnosis process of the above embodiment, the abnormality diagnosis parameter is based on the relationship between the change of increase in the PM detection voltage Vpm and the change of increase in the heater resistance directly after the start of energization of the heater, but may be modified. In short, the change in temperature of the heater 35 may be detected, and the information on the change in temperature may be used. Specifically, a power input into the heater after the start of energization of the heater, a heater power integrated value, a heater temperature, the temperature of the insulating substrate 32 (element temperature), and the like may be obtained as information about temperature change. The diagnosis of abnormality of the PM sensor 17 may be performed based on the relationship between any one of pieces of the above temperature change information and the change in the PM detection voltage Vpm.

In the forcible burning of the PM, the temperature of the PM sensor 17 at the time of start (at the start of energization of the heater) may be determined, and based on the determined temperature, at least one of the abnormality diagnosis parameter and the abnormality determination value may be corrected. Even when the sensor temperature changes at the start of energization of the heater 35, fluctuations in abnormality diagnosis parameter or abnormality determination value due to the sensor temperature can be eliminated, thus improving the accuracy of the abnormality diagnosis. Specifically, the information on temperature of the PM sensor 17 in use can include an element resistance (a resistance of an insulating substrate), a heater resistance, a power input into the heater, an integrated value of heater power, and the like.

In this embodiment, the heater 35 is provided in the insulating substrate 33 of the PM sensor 17 as heating means for the PM forcible burning. This arrangement may be modified. Specifically, measures may be provided for heating the temperature of gas in an exhaust pipe to a temperature at which the PM can be burned (for example, of 650° C.). For example, the measures include means for increasing the temperature of gas exhausted from an engine, and means for increasing the temperature of the inside of the exhaust pipe by providing heating means, such as a heater in the exhaust pipe.

The PM sensor 17 may be disposed on at least one of the downstream and upstream sides of a PM filter provided in an engine exhaust pipe and adapted for collecting PM. Further, based on a detected value provided by the PM sensor 17, the timing of reproducing the PM filter may be controlled. Alternatively, or additionally, based on the detected value provided by the PM sensor 17, the diagnosis of abnormality of the PM filter may be carried out.

The above embodiment is applied, by way of example, to the direct-injection gasoline engine, but can be applied to other types of engines. For example, the invention uses a diesel engine (especially, a direct injection engine), and can be applied to the PM sensor provided in an exhaust pipe of the diesel engine. The amount of PM contained in other kinds of gas except for the exhaust gas from the engine may be detected.

Although the present invention has been fully described in connection with the above embodiments thereof with reference to the accompanying drawings, it is to be noted that various changes and modifications will become apparent to those skilled in the art.

According to an aspect of the present embodiments and modification, a sensor controller includes a heater 35 configured to heat an attachment portion (32) so as to burn and remove the particulate matter attached to the attachment portion, and abnormality diagnosis means for obtaining a sensor detection value from a particulate matter detection sensor 17 during a heating of the heater 35 and for performing diagnosis of abnormality of the particulate matter detection sensor 17 based on the obtained sensor detection value.

When particulate matter attached to the attachment portion is heated so as to burn and remove the particulate matter, as shown in FIG. 4, the change in resistance between the opposed electrodes 36a, 36b causes the sensor detection value (PM detection voltage Vpm) to temporarily increase in accordance with the start of heating, and then to decrease in accordance with the actual burning of the particulate matter. Based on such a behavior of the sensor detection value, the diagnosis of abnormality of the particulate matter detection sensor 17 is performed. In this case, it is possible to previously recognize how the sensor detection value in the normal state changes at the time of heating. Then, for example, the diagnosis of the presence or absence of abnormality of the sensor can be carried out by comparing with the actual sensor detection value with a reference detection value at the normal operation of the sensor. As a result, the abnormality of the particulate matter detection sensor can be appropriately detected.

For example, the sensor controller may include means for obtaining the sensor detection value for a time period in which the resistance between the pair of opposed electrodes decreases in accordance with a start of the heating of the heater. In this case, the abnormality diagnosis means performs the diagnosis of abnormality of the particulate matter detection sensor based on a rate of change in the sensor detection value for the time period in which the resistance between the electrodes decreases.

As designated by the period from the timing t1 to the timing t2 of FIG. 4, at the start of heating by the heater 35, the sensor detection value (PM detection voltage Vpm) increases due to a change in resistance between the electrodes 36a, 36b, which is the temperature property of the particulate matter. In this case, when the abnormality is caused in the particulate matter detection sensor 17, the rate of change in the sensor detection voltage after the start of heating the sensor 17 becomes different from a normal rate.

Thus, the presence or absence of abnormality of the particulate matter detection sensor 17 can be detected.

Specifically, a rate of change in the sensor detection value (increasing rate) directly after the start of heating may be calculated. By comparing the calculated rate of change with a predetermined rate of change in the normal state, the diagnosis of abnormality can be performed. Alternatively, an actual time period required for the sensor detection value to reach a predetermined value (upper limit) may be calculated. By comparing the calculated actual time period with a predetermined time period required in the normal state, the diagnosis of abnormality may be performed.

For example, a signal output circuit may be connected to the particulate matter detection sensor, and the sensor detection value may be changeable by the signal output circuit within a predetermined output range. The sensor controller may further include means for obtaining the sensor detection value while the sensor detection value changes in a state where a limit of the predetermined output range reaches after the start of the heating of the heater 35. In this case, the abnormality diagnosis means performs the diagnosis of abnormality of the particulate matter detection sensor based on the sensor detection value while the sensor detection value reaches the limit of the predetermined output range.

The signal output circuit may output a sensor detection signal, for example, by changing a sensor detection value in a range of voltage that is processable, for example, by a microcomputer. The temperature of particulate material increases to some degree after the start of heating of the heater 35. In this state, as indicated by the period from the timing t2 to the timing t4, the sensor detection value (PM detection voltage Vpm) reaches and holds the limit of the predetermined output range of the signal output circuit due to the change in resistance between the electrodes 36a, 36b depending on the temperature property of the particulate matter. In this case, when the abnormality is caused in the particulate matter detection sensor, the state in which the sensor detection value reaches the limit of the predetermined output range becomes different from the normal state, thereby detecting the presence or absence of abnormality of the particulate matter detection sensor.

Specifically, the sensor controller calculates a duration (holding time period) while the sensor detection value reaches the limit of the predetermined output range. The diagnosis of abnormality may be performed by comparing the calculated duration with a predetermined duration in the normal state. Alternatively, the sensor controller may calculate a time when the sensor detection value reaching the limit of the predetermined output range begins to change toward the tendency to increase the resistance between the pair of opposed electrodes 36a, 36b. The diagnosis of abnormality may be performed by comparing the calculated time with a predetermined time in the normal state. Further, for a time period while the sensor detection value reaches the limit of the predetermined output range, the diagnosis of abnormality can be performed by comparing the limit in the normal state with the sensor detection value.

Furthermore, the sensor controller may include means for obtaining the sensor detection value for a time period in which the resistance between the pair of electrodes changes to increase in accordance with the particulate matter being burned and removed after the start of the heating of the heater. In this case, the abnormality diagnosis means performs the diagnosis of abnormality of the particulate matter detection sensor, based on a rate of change in the sensor detection value for the time period in which the resistance between the opposed electrodes 36a, 36b changes to increase.

Specifically, the sensor controller may calculate the rate of change (e.g., decreasing rate) in sensor detection value after the actual start of burning the particulate matter. The diagnosis of abnormality may be performed by comparing the calculated rate of change with a predetermined rate of change in the normal state. Alternatively, the sensor controller may calculate an actual time period required until the sensor detection value reaches the predetermined value (origin). The diagnosis of abnormality may be performed by comparing the calculated actual time required with a predetermined time required in the normal state.

For example, the abnormality diagnosis means performs the diagnosis of abnormality of the particulate matter detection sensor based on the time period required from the start of the heating of the heater 35 until the sensor detection value returns to the initial value.

As indicated by the period from the timing t1 to the timing t5 shown in FIG. 4, after the start of heating by the heater 35, the sensor detection value (PM detection voltage Vpm) temporarily increases, then decreases, and returns to the initial value (origin). In this case, when the abnormality is caused in the particulate matter detection sensor, the change in sensor detection value in a series of burning processes becomes different from that in the normal state. Thus, the period of time required until the sensor detective value returns to the initial value (origin) after the start of heating becomes different from the normal time period.

The heater 35 may include a heating element which is heated by energization. In this case, the sensor controller may further include: means for detecting a change in temperature of the heating element; and means for obtaining the sensor detection value and information on the change in temperature of the heating element during the time period while the resistance between the pair of opposed electrodes changes to decrease in accordance with the start of the heating of the heater 35. Furthermore, the abnormality diagnosis means may perform the diagnosis of abnormality of the particulate matter detection sensor based on relationship between the change in the sensor detection value and the information on the change in the temperature of the heating element for the time period while the resistance between the electrodes 36a, 36b changes to decrease.

At the start of burning by the burning means, as indicated by the period from the timing t1 to the timing t2 shown in FIG. 4, the heater resistance increases as the information on change in temperature of the heating element, and the sensor detective value (PM detection voltage Vpm) increases due to the change in resistance between the pair of opposed electrodes in accordance with the generated heat. In this case, when the abnormality is caused in the particulate matter detection sensor, the relationship between the change in the sensor detection value and the change in the resistance of the heating element becomes different from that at the normal time. This can detect the presence or absence of abnormality of the particulate matter detection sensor.

Specifically, the sensor controller calculates the rate in change of the sensor detection value and the rate in change of resistance of the heating element directly after the start of heating. By comparing the ratio between both change rates with a predetermined ratio of rate in the normal state, the diagnosis of abnormality may be performed.

The sensor controller may further includes means for obtaining another sensor detection value at a start of the heating of the heater 35, and means for correcting at least one of the abnormality diagnosis parameter and the abnormality determination value based on the sensor detection value obtained at the start of the heating.

For example, after the start of heating by the heater 35, as indicated by the period from the timing t1 to the timing t2 shown in FIG. 4, when the sensor detection value (PM detection voltage Vpm) increases, the rate of increase changes according to the level (e.g., voltage level) of the sensor detection value at the start of heating, i.e., according to the amount of the particulate matter attached to the attachment portion. Additionally, a duration of the time (holding time period) that the sensor detection value holds the limit of the predetermined output range also changes according to the level (voltage level) of the sensor detection value at the start of heating, in other words, according to the amount of particulate matter attached to the attachment portion.

From this point, at least one of the abnormality diagnosis parameter and the abnormality determination value is corrected based on the sensor detection value obtained at the start of heating. Thus, even when the level (voltage level) of the sensor detection value at the start of heating fluctuates, the accuracy of diagnosis of the abnormality can be improved.

Such changes and modifications are to be understood as being within the scope of the present invention as defined by the appended claims.

What is claimed is:

1. A sensor controller applied to a particulate matter detection sensor, the particulate matter detection sensor including an attachment portion to which conductive particulate matter contained in gas is attached, and a pair of opposed electrodes spaced from each other at the attachment portion, the particulate matter detection sensor being adapted to output a sensor detection value corresponding to a resistance of the particular matter between the pair of opposed electrodes, the sensor controller being adapted to calculate an amount of attached particulate matter based on the sensor detection value from the particulate matter detection sensor, the sensor controller comprising:
   a heater configured to heat the attachment portion so as to burn and remove the particulate matter attached to the attachment portion;
   abnormality diagnosis means for obtaining the sensor detection value outputted from the particulate matter detection sensor during a heating of the heater, and for performing diagnosis of abnormality of the particulate matter detection sensor; and
   means for storing the sensor detection value as a reference value after the heating of the heater starts, wherein the sensor detection value is stored as the reference value upon the resistance between the pair of electrodes changing to increasing in accordance with the particulate matter being burned and removed during the heating of the heater,
   wherein the abnormality diagnosis means calculates a rate of change in the sensor detection value during a time period in which the resistance between the opposed electrodes is increasing during the heating of the heater, wherein
   the abnormality diagnosis means calculates a reference rate based on the stored reference value, and
   the abnormality diagnosis means performs the diagnosis of abnormality of the particulate matter detection sensor by comparing the calculated rate of the change in the sensor detection value to the calculated reference rate.

2. A system comprising:

a particulate matter detection sensor, the particulate matter detection sensor including an attachment portion to which conductive particulate matter contained in gas is attached, and a pair of opposed electrodes spaced from each other at the attachment portion, the particulate matter detection sensor being configured to output a sensor detection value corresponding to a resistance of the particular matter between the pair of opposed electrodes;

a heater configured to heat the attachment portion so as to burn and remove the particulate matter attached to the attachment portion; and an electronic control unit configured to:

calculate an amount of attached particulate matter based on the sensor detection value from the particulate matter detection sensor;

obtain the sensor detection value outputted from the particular matter detection sensor during a heating of the heater;

perform diagnosis of abnormality of the particulate matter detection sensor;

store the sensor detection value as a reference value after the heating of the heater starts wherein the sensor detection value is stored as the reference value upon the resistance between the pair of electrodes changing to being increased in accordance with the particulate matter being burned and removed during the heating of the heater;

calculate a rate of change in the sensor detection value during a time period in which the resistance between the opposed electrodes is increasing during the heating of the heater, calculate a reference rate based on the stored reference value, and wherein the electronic control unit performs the diagnosis of abnormality of the particulate matter detection sensor by comparing the calculated rate of the change in the sensor detection value to the calculated reference rate.

3. The sensor controller according to claim 1, wherein one of the pair of opposed electrodes is connected to a sensor power supply, the other of the pair of opposed electrodes is connected to the resistor, the particulate matter detection sensor outputs a voltage at an intermediate point between the other of the pair of opposed electrodes and the resistor as the sensor detection value, and the abnormality diagnosis means performs the diagnosis of the particulate matter detection sensor, based on a rate of decrease in the sensor detection value for the time period in which the resistance between the opposed electrodes changes to increase.

4. The sensor controller according to claim 1, wherein the abnormality diagnosis means performs the diagnosis of abnormality of the particulate matter detection sensor during a heating of the heater only.

5. The system according to claim 2, wherein the electronic control unit performs the diagnosis of abnormality of the particulate matter detection sensor during a heating of the heater only.

6. The sensor controller according to claim 1, wherein the storing means stores the sensor detection value as the reference value upon the resistance between the pair of electrodes changing from remaining steady during the heating of the heater to increasing during the heating of the heater.

7. The sensor controller according to claim 1, wherein the resistance between the pair of electrodes, during the heating of the heater, decreases and then increases.

* * * * *